US008999672B2

(12) United States Patent
Williams (10) Patent No.: US 8,999,672 B2
(45) Date of Patent: Apr. 7, 2015

(54) COMPOSITIONS AND PROCESSES FOR IMPROVED PLASMID DNA PRODUCTION

(76) Inventor: James A. Williams, Lincoln, NE (US)

( * ) Notice: Subject to any disclaimer, the term of this patent is extended or adjusted under 35 U.S.C. 154(b) by 1005 days.

(21) Appl. No.: 11/814,294

(22) PCT Filed: Jan. 27, 2006

(86) PCT No.: PCT/US2006/003148
§ 371 (c)(1),
(2), (4) Date: Jul. 19, 2007

(87) PCT Pub. No.: WO2006/081529
PCT Pub. Date: Aug. 3, 2006

(65) Prior Publication Data
US 2010/0167358 A1 Jul. 1, 2010

Related U.S. Application Data

(60) Provisional application No. 60/647,863, filed on Jan. 28, 2005.

(51) Int. Cl.
*C12P 19/34* (2006.01)
*C07H 21/04* (2006.01)
*C12N 15/00* (2006.01)
*C12N 15/10* (2006.01)
*C12N 15/64* (2006.01)
*C12N 15/69* (2006.01)
*C12N 15/70* (2006.01)

(52) U.S. Cl.
CPC ............... *C12N 15/10* (2013.01); *C12N 15/64* (2013.01); *C12N 15/69* (2013.01); *C12N 15/70* (2013.01)

(58) Field of Classification Search
None
See application file for complete search history.

(56) References Cited

U.S. PATENT DOCUMENTS

| | | | |
|---|---|---|---|
| 4,703,012 A | 10/1987 | Boros et al. | |
| 5,015,573 A | 5/1991 | Yarranton et al. | |
| 5,561,064 A | 10/1996 | Marquet et al. | |
| 5,616,459 A * | 4/1997 | Kramer et al. | 435/5 |
| 6,294,372 B1 | 9/2001 | Burian et al. | |
| 6,806,066 B2 | 10/2004 | Bayer et al. | |

OTHER PUBLICATIONS

Tomizawa et al (Proc. Nat. Acad. Sci. USA 78(10): 6096-6100, 1981).*
Angelov et al, Amplification of Bacterial Plasmids Without Blocking Protein Biosynthesis, 1989, Plasmid, Short Communications, vol. 22, pp. 160-162.
Bachvarov et al, Construction of a ColE1 Plasmid Bearing Inducible High-Copy-Number Phenotype, 1990, Folia Microbiology, vol. 35, pp. 177-182.
Bert et al, Generation of an Improved Luciferase Reporter Gene Plasmid That Employs a Novel Mechanism for High-Copy Replication, 2000, Plasmid, vol. 44, pp. 173-182, Academic Press.
Binnie et al, Absence of RNase III Alters the Pathway by which RNAI, the Antisense Inhibitor of Col1 Replication, Decays, 1999, Microbiology, vol. 145, pp. 3089-3100.
Birnboim et al, A Rapid Alkaline Extraction Procedure for Screening Recombinant Plasmid DNA, 1979, Nucleic Acids Research, vol. 7, No. 6, pp. 1513-1523.
Boros et al, High-Copy-Number Derivatives of the Plasmid Cloning Vector pBR322, 1984, Gene, vol. 30, pp. 257-260.
Carnes, Fermentation Design for the Manufacture of Therapeutic Plasmid DNA, Oct. 2005, BioProcess International Technical, pages 2-7.
Datsenko et al, One-Step Inactivation of Chromosomal Genes in *Escherichia coli* K-12 Using PCR Products, Jun. 6, 2000, PNAS, vol. 97, No. 12, pp. 6640-6645.
Diaz et al, The Two-Step Lysis System of *Pneumococcal bacteriophage* EJ-1 is Functional in Gram-Negative Bacteria: Triggering of the Major Pneumococcal Autolysin in *Escherichia coli*, 1996, Molecular Microbiology, vol. 19, No. 4, pp. 667-681.
Fassier et al, Reduced Superhelicity of Plasmid DNA Produced by the rho-15 Mutation in *Escherichia coli*, 1986, Mol Gen Genet, vol. 204, pp. 424-429.
Ferber et al, Combinatorial Selection of a Small RNA that Induces Amplification of IncFII Plasmids in *Escherichia coli*, 1998, Journal of Mol Biol, vol. 279, pp. 565-576.
Fitzwater et al, Conditional High Copy Number ColE1 Mutants: Resistance to RNA1 Inhibition in vivo and in vitro, 1988, The EMBO Journal, vol. 7, No. 10, pp. 3289-3297.
Franch et al, Antisense RNA Regulation in Prokaryotes: Rapid RNA/RNA Interaction Facilitated by a General U-turn Loop Structure, 1999, Journal Mol Biol, vol. 294, pp. 1115-1125.
Grabherr et al, Stabilizing Plasmid Copy Number to Improve Recombinant Protein Production, Jan. 20, 2002, Biotechnology and Bioengineering, vol. 77, No. 2, pp. 142-147.
Gultyaev et al, The Influence of a Metastable Structure in Plasmid Primer RNA on Antisense RNA Binding Kinetics, 1995, Nucleic Acids Research, vol. 23, No. 18, pp. 3718-3725.
Harinarayanan et al, Host Factor Titration by Chromosomal R-Loops as a Mechanism for Runaway Plasmid Replication in Transcription Termination-defective Mutants of *Escherichia coli*, 2003, Journal Molecular Biology, vol. 332, pp. 31-46.
Hofmann et al, Amplification of pBR322 Plasmid DNA in *Escherichia coli* relA Strains During Batch and Fed-Batch Fermentation, 1990, Journal of Basic Microbiology, vol. 30, pp. 37-41.
Kolb et al, Progression of a Loop-Loop Complex to a Four-Way Junction is Crucial for the Activity of a Regulatory Antisense RNA, 2000, The EMBO Journal, vol. 19, No. 21, pp. 5905-5915.
Lin-Chao et al, The Rate of Processing and Degradation of Antisense RNAI Regulates the Replication of ColE1-Type Plasmids in Vivo, Jun. 28, 1991, Cell, vol. 65, pp. 1233-1242.
Lin-Chao et al, Activities of the RNAI and RNAII Promoters of Plasmid pBR322, Mar. 1987, Journal of Bacteriology, vol. 169, No. 3, pp. 1217-1222.
Lin-Chao et al, High Copy Number of the pUC Plasmid Results from a Rom/Rop-Suppressible Point Mutation in RNAII, 1992, Molecular Microbiology, vol. 6, No. 22, pp. 3385-3393.

(Continued)

*Primary Examiner* — Richard Schnizer (57) ABSTRACT

Improvements in plasmid DNA production technology are needed to insure the economic feasibility of future DNA vaccines and DNA therapeutics. General methods are described, by means of which it is possible to dramatically increase plasmid DNA productivity. These processes feature RNA based inducers of plasmid copy number.

2 Claims, 4 Drawing Sheets

(56) References Cited

OTHER PUBLICATIONS

Magliery et al, A Cell-Based Screen for Function of the Four-Helix Bundle Protein Rop: A New Tool for Combinatorial Experiments in Biophysics, 2004, Protein Engineering, Design & Selection, vol. 17, No. 1, pp. 77-83.

Makrides, Strategies for Achieving High-Level Expression of Genes in *Escherichia coli*, Sep. 1996, Microbiological Reviews, vol. 60, No. 3, pp. 512-538.

Masse et al, *Escherichia coli* DNA Topoisomerase I Inhibits R-Loop Formation by Relaxing Transcription-Induced Negative Supercoiling, 1999, The Journal of Biological Chemistry, vol. 274, No. 23, pp. 16659-16664.

Mermod et al, Vector for Regulated Expression of Cloned Genes in a Wide Range of Gram-Negative Bacteria, Aug. 1986, Journal of Bacteriology, vol. 167, No. 2, pp. 447-454.

Mohanty et al, Polyadenylation of *Escherichia coli* Transcripts Plays an Integral Role in Regulating Intracellular Levels of Polynucleotide Phosphorylase and RNase E, 2002, Molecular Microbiology, vol. 45, No. 5, pp. 1315-1324.

Moser et al, Characterization and Complementation of mPB1 Copy Number Mutant: Effect of RNA I Gene Dosage on Plasmid Copy Number and Incompatibility, May 1983, Journal of Bacteriology, vol. 154, No. 2, pp. 809-818.

Murphy, Use of Bacteriophage 'Lamda' Recombination Functions to Promote Gene Replacement in *Escherichia coli*, Apr. 1998, Journal of Bacteriology, vol. 180, No. 8, pp. 2063-2071.

Neidhardt et al, Culture Medium for *Enterobacteria*, Sep. 1974, Journal of Bacteriology, vol. 119, No. 3, pp. 736-747.

Operschall et al, Mechanism of Protection Against Influenza A Virus by DNA Vaccine Encoding the Hemagglutinin Gene, 2000, Intervirology, vol. 43, pp. 322-330.

Sarkar et al, Identification of Multicopy Suppressors of the pcnB Plasmid Copy Number Defect in *Escherichia coli*, 2002, Mol Genet Geomics, vol. 268, pp. 62-69.

Schroeter et al, Amplification of Different ColE1 Plasmids in an *Escherichia coli* relA Strain, 1988, Journal of Basic Microbiology, vol. 28, No. 8, pp. 553-555.

Shishido et al, Increasing Production of a Knotted Form of Plasmid pBR322 DNA in *Escherichia coli* DNA Topoisomerase Mutants, 1987, Journal of Molecular Biology, vol. 195, pp. 215-218.

del Solar et al, Replication and Control of Circular Bacterial Plasmids, Jun. 1998, Microbiology and Molecular Biology Reviews, vol. 62, No. 2, pp. 434-464.

Tao et al, Isolation of Chromosomal Mutations That Affect Carotenoid Production in *Escherichia coli*: Mutations Alter Copy Number of ColE1-Type Plasmids, 2005, FEMS Microbiology Letters, vol. 243, pp. 227-233.

Teich et al, Amplification of ColE1 Related Plasmids in Recombinant Cultures of *Escherichia coli* After IPTG Induction, 1998, Journal of Biotechnology, vol. 64, pp. 197-210.

Wagner et al, Kissing and RNA Stability in Antisense Control of Plasmid Replication, Dec. 1998, Trends in Biochemical Sciences, vol. 23, issue 12, pp. 451-454.

Wang et al, A Model for Regulation of CoiE1-Like Plasmid Replication by Uncharged tRNAs in Amino Acid-Starved *Escherichia coli* Cells, 2002, Plasmid, vol. 47, pp. 69-78.

Wegrzyn, Replication of Plasmids During Bacterial Response to Amino Acid Starvation, 1999, Plasmid, vol. 41, pp. 1-16.

Wong et al, Temperature-Sensitive Copy Number Mutants of ColE1 are Located in an Untranslated Region of the Plasmid Genome, Jun. 1982, Proc Natl Acad Sci USA, vol. 79, pp. 3570-3574.

Wright et al, Dual-Origin Plasmids Containing an Amplifiable ColE1 ori; Temperature-Controlled Expression of Cloned Genes, 1986, Gene, vol. 49, pp. 311-321.

Xu et al, The *Escherichia coli* pcnB Gene Promotes Adenylylation of Antisense RNAI of ColE1-type Plasmids in vivo and Degradation of RNAI Decay Intermediates, Jul. 1993, Proc Natl Acad Sci USA, vol. 90, pp. 6756-6760.

Xu et al, Polyadenylation Can Regulate ColE1 Type Plasmid Copy Number Independently of Any Effect on RNAI Decay by Decreasing the Interaction of Antisense RNAI with its RNAII Target, 2002, Plasmid, vol. 48, pp. 49-58.

Yavachev et al, What Does the Homology Between *E. coli* tRNAs and RNAs Controlling ColE1 Plasmid Replication Mean?, 1988, Journal of Theor Biology, vol. 131, pp. 235-241.

Zuker, Mfold Web Server for Nucleic Acid Folding and Hybridization Prediction, 2003, NucleicAcids Research, vol. 31, No. 13, pp. 3406-3415.

Carnes, Fermentation Design for the Manufacture of Therapeutic Plasmid DNA, Oct. 2005, Bioprocess International, vol. 3, No. 9, pp. 36-44.

US Department of Health and Human Services, FDA, Center for Biologics Evaluation and Research, Points to Consider on Plasmid DNA Vaccines for Preventive Infectious Disease Indications, 1996.

US Department of Health and Human Services, FDA, Center for Biologics Evaluation and Research, Points to Consider in the Characterization of Cell Lines Used to Produce Biologies, 1993.

Kwong, M. Stephan et al., *Staphylococcus aureus* multiresistance plasmid pSK41: analysis of the replication region, initiator protein binding and antisense RNA regulation. Molecular Microbiology. Jan. 2004, vol. 51, No. 2 pp. 497-509.

* cited by examiner

COMPOSITIONS AND PROCESSES FOR IMPROVED PLASMID DNA PRODUCTION

This application claims the benefit of Provisional Patent Application Ser. No. 60/647,863 filed 28 Jan. 2005.

STATEMENT REGARDING FEDERALLY SPONSORED RESEARCH OR DEVELOPMENT

This invention was made in part with government support under Grant No. 1 R43GM073394-01, awarded by the National Institutes of Health. The government has certain rights in this invention.

FIELD OF THE INVENTION

The present invention relates to the production of covalently closed circular (ccc) recombinant DNA molecules such as plasmids, cosmids, bacterial artificial chromosomes (BACs), bacteriophages, viral vectors and hybrids thereof, and more particularly is a method for inducing production of the said DNA molecules to high levels.

BACKGROUND OF THE INVENTION

The present invention relates to the production of covalently closed circular (ccc) recombinant DNA molecules. Such molecules are useful in biotechnology, transgenic organisms, gene therapy, therapeutic vaccination, agriculture and DNA vaccines.

With the invention in mind, a search of the prior art was conducted. E. coli plasmids have long been the single most important source of recombinant DNA molecules used by researchers and by industry. Today, plasmid DNA is becoming increasingly important as the next generation of biotechnology products (gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines. Plasmids are also utilized in gene therapy or gene replacement applications, wherein the desired gene product is expressed from the plasmid after administration to the patient.

The basic methods for obtaining plasmids (by bacterial fermentation), and for their purification (e.g., by the alkaline lysis method (Birnboim, H C, Doly J. 1979, *Nucleic Acids Res.* 7: 1513-1523)) are well-known.

The use of reduced growth rate is the unifying principle in high quality, high yield plasmid fermentations. The optimal temperature for E. coli growth is 37° C. However, lower temperatures (30-37° C.) may be used in batch fermentation to cause a reduced maximum specific growth rate. Higher temperatures (36-45° C.) can also be employed to induce selective plasmid amplification with some replication origins such as pUC (Lin-Chao S, Chen W T, Wong T T. 1992 *Mol. Microbiol.* 6: 3385-3393), and pMM1 (Wong E M, Muesing M A, Polisky, B. 1982 *Proc Natl Acad Sci USA.* 79: 3570-3574) (Reviewed by Carnes A E. 2005 *BioProcess International* 3: 36-44).

The fermented bacterial cell paste is then resuspended and lysed (using a combination of sodium hydroxide and sodium dodecylsulfate), after which the solution is neutralized by the addition of acidic salt (e.g., potassium acetate), which precipitates the bacterial DNA and the majority of cell debris. The bulk of super-coiled plasmid DNA remains in solution, along with contaminating bacterial RNA, DNA and proteins, as well as E. coli endotoxin (lipopolysaccharide, or LPS). The soluble fraction is then separated by filtration and subjected to a variety of purification steps, which may include: RNase digestion; chromatography (ion exchange gel filtration, hydroxyapatite, gel filtration, hydrophobic interaction, reverse phase, HPLC, etc.); diafiltration; organic extraction, selective precipitation, etc.

Today, the FDA standards are not defined except in preliminary form (see: FDA Points to Consider on Plasmid DNA Vaccines for Preventive Infectious Disease Indications, 1996). However, in the future, international standards for plasmid DNA purity are likely to be the same or very similar to those that are used for recombinant protein products similarly produced from E. coli fermentation, and such standards exceed the current purity attainable from established methods. Most glaringly, the accepted standard of <100 pg host genomic DNA per dose (see: FDA Points to consider in the characterization of cell lines used to produce biologics, 1993) is far below the levels currently attainable for purified plasmid preparations (100 pg per 1 mg dose is equivalent to one part per ten million).

Clearly, increasing the purity of the starting material through improved yield would improve the final product purity, and ultimately is an important goal to facilitate the manufacture of clinical grade DNA on an industrial scale.

High Copy Replication Origins

Circular plasmids of bacteria replicate by theta, strand displacement or Rolling circle mechanisms (see Del Solar G, Giraldo R, Ruiz-Echevarria, Espinosa M, and Diaz-Orejas R. 1998 *Microbiol. Molec. Biol. Reviews* 62: 434-464 for a comprehensive review).

To date, all therapeutic plasmids (e.g. for gene therapy or vaccination) utilize theta replication origins. Theta replication requires synthesis of a primer RNA, and DNA synthesis is initiated by extension of the RNA primer. This type of replication is characterized by the separation of the DNA strands at the origin creating a characteristic theta-shaped replication bubble.

Most theta replication plasmids such as R6K (used in pCOR therapeutic plasmid), R1 or pKL1 (but not pMB1 or ColE1 derived; see below) require a plasmid-encoded Rep initiator protein which binds to specific sequences (often tandem direct repeats called iterons) in the replication origin and recruit host DnaA initiator protein to flanking dnaA box. In contrast, pMB1 and ColE1 plasmids produce a RNAII primer that is cleaved by RNase H, and extended by DNA polymerase I prior to switching to DNA polymerase III.

Origin Biology: ColE1 Type Origin

Figure 1:
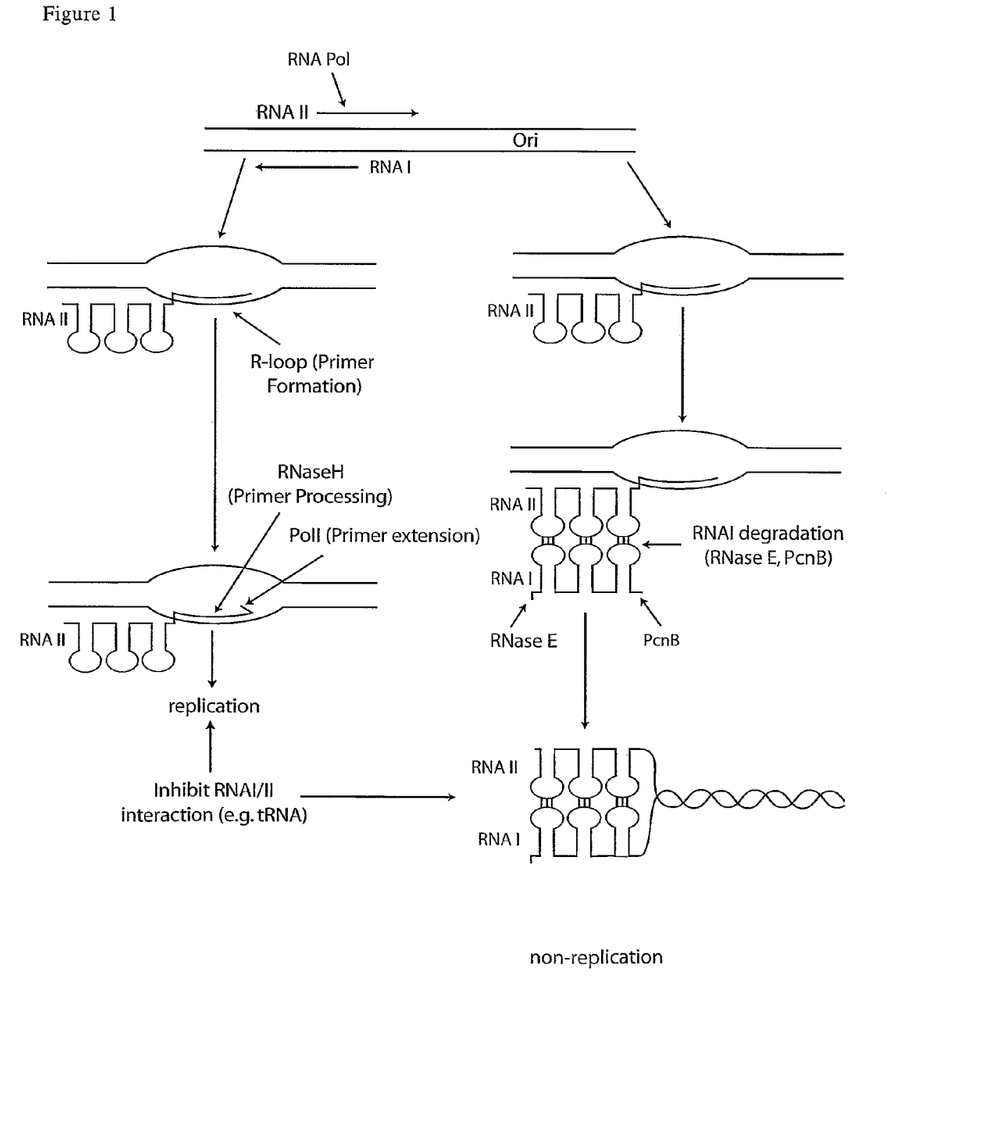
FIG. 1 shows the replication of high copy (Rom-) ColE1 plasmids.

The vast majority of therapeutic plasmids currently in use are derived from pBR322 or pUC plasmids, and use high copy derivatives of the pMB1 origin (closely related to the ColE1 origin). For example, pcDNA3, VR1012, pVAX1, pVC0396, DNA vaccine plasmids utilize the pMB1 derived pUC origin, pVC0396 uses the ColE1 derived pMM1 origin, while the pCMVkm2 DNA vaccine plasmid utilizes the pMB1 derived ROP-pBR322-derived origin. The ColE1 type (ColE1) plasmid copy number is controlled by RNAI, an antisense RNA (FIG. 1; reviewed in Del Solar et al, Supra, 1998). RNAI forms a tRNA like structure, with three stem loops. The 5' end of the primer, RNAII, is complementary to RNAI and forms a three loop structure antisense to RNAI. The RNAI interaction initiates at the complementary unpaired loops in RNAII (kissing interaction; reviewed in Wagner E G H, Brand S. 1998 *TIBS* 23: 451-454) preventing its maturation into the replication primer. The loop regions contain YUNR (Y=pyrimidine R=purine) motifs that specify two intraloop hydrogen bonds forming U-turn structures. This motif is present in the loops in natural antisense RNA regulated systems including RNAI and RNAII, and is speculated to be an enhancer of RNA pairing rates (Franch T, Petersen M, Wagner E G H, Jacobsen J P, Gerdes K. 1999 *J Mol Biol* 294:1115-1125). Analysis of copy number mutants isolated in the RNAI/RNAII overlap region indicates the importance of at least loops 2 and 3 in repression (Moser D R, Campbell J L. 1983 *J Bacteriol* 154: 809-818). The RNAI/II interaction is stabilized, and potentially protected from RNase degradation by the repressor of primer (ROP or ROM) protein and destabilized by uncharged tRNAs (see below). There is a short window of opportunity for the RNAI/II interaction, as RNAII changes conformation as it forms the primer, becoming inaccessible to RNAI. Maturation of the primer requires RNaseH cleavage, and primer extension by DNA polymerase I before switching to DNA polymerase III (FIG. 1). RNAI is constitutively synthesized to high levels relative to RNAII, but is degraded rapidly. RNAI inhibition is efficient; it is estimated that in the wild type origin (i.e. pBR322) at most 5% of RNAII transcripts are processed into an active primer (Lin-Chao S, Bremer H. 1987 *J Bacteriol.* 169:1217-1222).

The rate of processing and degradation of RNAI regulates ColE1 plasmid copy number (Lin-Chao S, Cohen S N. 1991. *Cell* 65:1233-1242). RNase E is the primary endogenous RNase that degrades RNAI to the unstable RNAI$_5$ (FIG. 1). Polyadenylation of RNAI by polyA polymerase (pcnB gene product) reduces affinity for RNAII (Xu F F, Gaggero C, Cohen S N. 2002 *Plasmid* 48:49-58) and enhances RNAI degradation by RNase E (Xu F, Lin-Chao S, Cohen S N. 1993 *Proc. Natl. Acad. Sci.* 90:6756-6760). RNaseIII also contributes to RNAI degradation (see Binnie U, Wong K, McAteer S, Masters M. 1999 *Microbiology* 145:3089-3100 for a review of RNAI degradation pathways) as does polynucleotide phosphorylase.

High Copy Number Replicons:

Inducible plasmid copy number replication origins are preferred for therapeutic plasmids. This is because constitutive high plasmid levels increases metabolic burden on the cells, and may result in instability, lower productivity or toxicity to cells. Mechanisms for creation of conditional high copy plasmids, and conditional runaway replicons, are discussed below.

ColEI type origin: Numerous copy up versions of the ColEI and pMB1 origins have been isolated, as either spontaneous or selected mutations (in screens for temperature sensitive resistance to extreme levels of antibiotic). The lesions associated with several high-copy number mutants are clustered in the RNAI promoter but do not affect RNAI transcription. Rather, they appear to affect the secondary structure of the RNAII replication primer that may either affect RNAI/RNAII interactions or the ability of RNAI to inhibit replication initiation (Lin-Chao et al, Supra, 1992; Fitzwater T, Zhang X, Bible R, Polisky B. 1988 *EMBO J.* 7:3289-3297; Gultyaev A P, Batenburg F H D, Pleij C W A. 1995 *Nuc Acids Res* 23:3718-3725). Commonly utilized copy up derivatives of the pMB1 origin (e.g. pUC19; Lin-Chao et al, Supra, 1992) or ColE1 origin (pMM1, pMM7; Wong et al, Supra, 1982) delete the accessory ROP (rom) protein and have an additional alteration that destabilizes the RNAI/RNAII interaction. For temperature sensitive origins (e.g. pUC, pMM1, pMM7), shifting of the culture from 30 to 42° C. leads to 30-40 fold increase in plasmid copy number to 300 copies per cell. Many of these derivatives are maximally induced by both temperature and entry into stationary phase (pMM1, pMM7, pUC; Lin-Chao et al, Supra, 1992; Fitzwater et al, Supra, 1988; Wong et al, Supra, 1982). pMM7 is reported to have 119 copies per cell in early log, and undergo a further 21 fold increase in copy number by late stationary phase. In stationary phase, pMM7 plasmid DNA accounts for >50% of total cell DNA (Fitzwater et al, Supra, 1988).

Other pMB1 copy number mutations have been identified. For example, the pXPG mutation changes the −10 region of the RNAII promoter from TAATCT to TAATAT, which may increase the expression of RNAII (Bert A G, Burrows J, Osborne C S, Cockerill P N. 2000 *Plasmid* 44:173-182). This increases the copy number of pBR322 at low temperature. Derivatives that over-express RNAII conditionally at high temperature (using an inducible promoter) have been rationally designed to increase copy number. For example, dual origin plasmids with ColE1 RNAII expression driven by $\lambda P_R$ promoter increase plasmid copy number from 3-4 at 30° C. to 200-300 at 42° C. (Wright E M, Humphreys G O, Yarranton G T. 1986 *Gene* 49: 311-321; Yarranton, G T, Humphreys, G O, Robinson, M K, Caulcott, C A, Wright E M. 1991 U.S. Pat. No. 5,015,573).

A nonconditional mutation at the 3' end of RNAI in pBR322 results in a copy number of 1000 per cell or 65% of total cellular DNA; this mutation is also associated with toxicity, due to its constitutive nature (Boros I, Posfai G, Venetianer P. 1984 *Gene* 30:257-260; Boros I, Venetianer P, Posfai G. 1984 U.S. Pat. No. 4,703,012).

As well, a pBR322 plasmid was modified to produce a truncated RNAII driven by a inducible synthetic promoter (in addition to native RNAII); this increased the copy number of pBR322 four fold upon induction, possibly due to inhibition of RNAI by the truncated RNAII (Bachvarov D, Jay E, Ivanov I. 1990 *Folia Microbiol* 35:177-182).

Alterations to RNAI and RNAII loop 2 by random mutagenesis, followed by selection for colonies exhibiting high levels of antibiotic resistance, was used to isolate high copy number variants of pET11a-SOD (pBR322 origin). These variants exhibit 14 fold increase in copy number, which is further increased up to 2500 plasmids/cell by IPTG induction of the T7 promoter driven SOD gene (Bayer K, Grabherr R, Nisson E, Striedner G. 2004 U.S. Pat. No. 6,806,066B2). The uninduced increases may be due to decreased affinity in RNAI/RNAII binding due to elimination of the RNA/RNA interaction enhancing YUNR U-turn structures. The induction after IPTG addition may be due to protein synthesis inhibition, and therefore be similar to copy number amplification after chloramphenicol treatment (Teich A, Lin H Y, Andersson L, Meyer S, Neubauer P. 1998 *J Biotechnol* 64:197-210).

A major disadvantage with all these modified high copy replicons is that they cannot be utilized to improve yield of existing plasmids without reengineering. Retrofitted plasmids would require reevaluation of the biological activity and safety, since new sequences may alter the immunogenicity or expression of a target gene from the plasmid.

Increasing Plasmid Copy Number without Alteration to Target Plasmid Sequences

Host strains with inducible factors that cause increased replication could improve productivity by a synergistic interaction with existing high copy ColE1 origins. Theoretically, such factors could participate in the plasmid replication pathway (FIG. 1) at several steps including:
1) Increase RNAI degradation (e.g. increased poly A polymerase or specific mRNA degradosome components such as RNaseE),
2) Inhibit RNAI interaction with RNAII (e.g. uncharged tRNA's)
3) Enhance primer formation (e.g. stabilize R loops; see below)

4) Enhance primer processing (e.g. increased RNaseH),
5) Increase initial DNA synthesis rates (e.g. increased DNA polymerase I)

Overexpression or repression of *E. coli* gene products on their own might not increase copy number due to the complexity of the regulatory pathways for each of these genes:
- gene product may be saturating, or not a limiting component of a complex
- gene product may by redundant
- gene product may be toxic at low or high levels or
- gene product overexpression may induce a compensatory effect.

For example, as expected, ColE1 plasmid copy number is decreased in RNaseE or PolyA polymerase mutants. However, increased polyadenylation by overexpression of pcnB, although increasing levels of RNaseE, does not increase plasmid copy number (Mohanty B K, Kushner S R. 2002 *Mol Micro* 45:1315-1324). Inactivation of genes involved in factor-dependent transcription termination, nusG or rho, leads to runaway lethal replication of ColE1 plasmids including pUC; the excess chromosomal R-loops in these strains are hypothesized to titrate R-loop destabilizing factors (i.e. possibly rnhA, RecG, DNA topoisomerase I, RNaseH; Harinarayanan R, Gowrishankar J. 2003 *J Mol Biol* 332:31-46). However, the quality of plasmids induced in this way may be altered. Topoisomerase is required to prevent plasmid knotting (Shishido K, Komiyama N, Ikawa S. 1987 *J Mol Biol* 195:215-218) remove R-loops (Masse E, Drolet M. 1999 *J Biol Chem* 274:16659-16664) and regulates plasmid supercoiling. As expected, plasmid DNA supercoiling is reduced in rho mutants (Fassier J S, Arnold G F, Tessman I. 1986 *Mol. Gen. Genet.* 204:424-429). In general, plasmid quality may be compromised with alteration of gene products involved in DNA replication, repair, recombination, supercoiling, or other pathways that are essential for plasmid integrity. Such systems may also self limit yield due to secondary toxicity (e.g. pcnB or RNaseE overexpression is toxic to the cell).

A variety of screens for copy number enhancing mutations have been performed, and yielded chromosomal mutations that increase plasmid copy number. Some of these mutations are speculated to alter antisense regulation of the plasmid in favor of higher copy number (for example, see Tao L, Jackson R E, Rouviere P E, Cheng Q. 2005 *FEMS Microbiol Lett.* 243:227-233). However, these screens have all been performed with relatively low copy number pBR322 based plasmids, and the utility of the identified mutations to increase copy number of higher copy number plasmids such as pUC have not been demonstrated.

Antisense regulation of copy number by uncharged tRNAs has been observed. Amino acid starvation leads to expression of the stringent (wild type) or relaxed (relA) response. In relA strains, uncharged tRNAs are elevated under conditions of amino acid limitation such as in starved stationary phase culture. Binding of the uncharged tRNAs to loops in RNAI and/or RNAII prevents RNAI interaction with RNAII, and increases plasmid copy number. This can increase copy number up to 10 fold in amino acid starved stationary phase cells versus log phase cells (pBR322 is amplified from 50 to 340; pUC9 is amplified from 90 to 940; Schroeter A, Riethdorf S, Hecker M. 1988 *J Basic Microbiol* 28:553-555). However, copy number is also increased in stationary phase cells by supplementation (rather than depletion) of amino acids (Angelov I, Ivanov I. 1989 *Plasmid* 22: 160-162), and is observed in RelA+ strains, so copy number increase in stationary phase is complex, with additional unknown mechanisms to increase copy number.

Stationary phase amplification due to amino acid depletion has been exploited to increase pBR322 yield in fermentation culture by depletion of arginine during batch or fed-batch growth (Hofinann K H, Neubauer P, Riethdorf S, Hecker M. 1990 *J Basic Microbiol* 30:37-41). However, the yield increase was modest (only 50 mg/L), was shown only with a moderate copy number plasmid (pBR322) and is not a generally useful process, since current optimal plasmid DNA fermentation processes that yield >100 mg plasmid/L use growth restriction to produce high levels of plasmid prior to stationary phase (Reviewed in Carnes, Supra, 2005).

Uncharged tRNA induction of plasmid copy number has been hypothesized to be through binding interaction with either the anticodon, dihydrouridylic loop (these interactions must be stabilized by an unknown mechanism in uncharged tRNAs) or 3' CCA-OH sequence of the tRNA, with complementary sequences in RNAI and RNAII loops (Yavachev L, Ivanov I. 1988 *J. Theor. Biol.* 131:235-241; Wang Z, Le G, Shi Y, Wegrzyn G, Wrobel B. 2002 *Plasmid* 47:69-78; reviewed in Wegrzyn G. 1999 *Plasmid* 41:1-16). Removal of the homology to tRNAs in RNAI and RNAII loop 2 by site directed mutagenesis eliminated copy number variation; this demonstrates that loop 2 is a key target (Grabherr R, Nilsson E, Striedner G, Bayer K. 2002 *Biotechnol Bioeng.* 2002; 77:142-147).

Overexpression of a naturally occurring antisense sequence may be responsible for repressing the copy number defect of a pBR322 plasmid in a pcnB mutant by interfering with RNAI activity through loop III (Sarkar N, Cao G, Jain C. 2002 *Mol Genet Genomics* 268: 62-69). However, the utility of this putative antisense regulator was not determined since induction of plasmid copy number was not demonstrated in a wild type background, nor was the method shown to have application for the production of high copy plasmids. A combinatorial selection scheme (using a low copy number reporter plasmid that produced a low level of a selective agent that was insufficient for cell survival, but increased levels would allow cells to grow) using random RNA expression plasmids identified an RNA that increased INcFII plasmid copy number (Ferber M J, Maher III J. 1998 *J Mol Biol.* 279:565:576); however, this methodology was not applied to improve copy number of high copy plasmids, or of ColE1 plasmids.

Collectively, none of the host strains or methods described above have been shown to have utility in improving yield of existing high copy plasmids.

Current Barriers

Many therapeutic plasmids are not inducible to maximal levels or contain detrimental sequences that limit plasmid copy number, limiting productivity yields. This may be overcome by increasing plasmid replication rate. Selection of new inducible replication origins that reach maximal levels in log phase (rather than late stationary phase) would be applicable for fermentation processing. However, a major disadvantage with engineering new runaway replicons is that they cannot be utilized to improve yield of existing plasmids without reengineering. Retrofitted plasmids would require reevaluation of the biological activity and safety, since new sequences may alter the immunogenicity or expression of a target gene from the plasmid.

Even in view of the prior art, there remains a need for a cost effective method to further increase plasmid DNA production. Fermentation processes which incorporate what is currently known in the art to improve plasmid productivity, such as reduced growth rate and plasmid copy number induction with high temperature can give yields exceeding 1 gm plasmid DNA/L with optimal high copy pUC origin plasmids (Reviewed in Carnes, Supra, 2005). Further yield increases would further reduce costs and improve final product purity. Moreover, alternative origins (e.g. pBR322 origin with ROP deletion) or non optimal pUC origin-containing plasmids may produce 1 or 2 orders of magnitude lower levels of plasmid. This low yield imposes a cost and purity burden on commercialization of plasmid DNA production processes using these vectors. Although economies of scale will reduce the cost of DNA significantly in the future, a far more economical solution to this problem is needed in order to achieve the desired cost. As well, international standards for plasmid DNA purity are likely to be the same or very similar to those that are used for recombinant protein products similarly produced from E. coli fermentation, and such standards exceed the current purity attainable from established methods. Increasing the yield (mg of DNA/gram of cell paste) in fermentation would both decrease the cost and increase the purity of the DNA (because it reduces the amount of material being processed).

DISCLOSURE OF THE INVENTION

The invention is a method for inducing production of ColE1-derived origin containing DNA replicons, utilizing anti-RNAI regulators. Specifically, a method of plasmid production is disclosed in which plasmid-containing E. coli cells are grown to accumulate biomass, followed by induction of anti-RNAI regulators, and continued growth in order to accumulate plasmid, whereby the anti-RNAI regulators improves yield of plasmid. In a preferred embodiment, the anti-RNAI regulators are antisense RNAs. In a preferred embodiment, the anti-RNAI regulators are induced by temperature shift. In another preferred embodiment, the anti-RNAI regulators are induced by chemical inducers. In another preferred embodiment, the chemical inducer is IPTG. In another preferred embodiment, the plasmid contains a ColE1-derived replication origin. In another preferred embodiment, the plasmid contains a pMB1-derived replication origin. In another preferred embodiment, the plasmid contains a pMB1-derived replication origin with an ROP gene deletion (ROP-pBR322 origin). In yet another preferred embodiment, the plasmid contains a pMB1 replication origin containing the pUC G to A mutation. These processes dramatically improve plasmid DNA yield, while maintaining or improving plasmid integrity, relative to the processes described in the art.

BRIEF SUMMARY OF THE INVENTION

It is a purpose and/or objective of the present invention to provide compositions and processes to improve plasmid DNA production yield.

Further objects and advantages of the invention will become apparent from a consideration of the drawings and ensuing description.

DETAILED DESCRIPTION OF THE INVENTION

Turning now to the drawings, FIG. 1, shows the replication of high copy (rop-) ColE1 plasmids. Critical steps/gene products that may affect copy number are shown.

Figure 2:
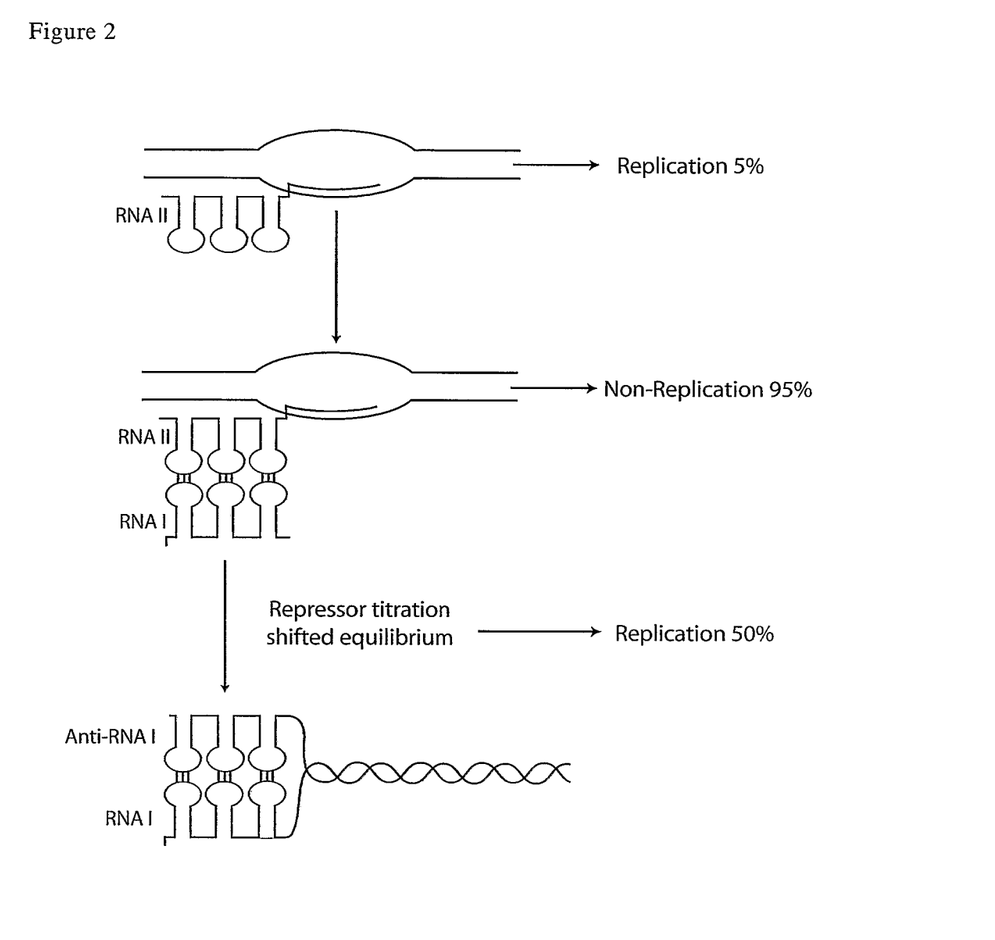
FIG. 2 shows Anti-RNAI induced plasmid replication.

In FIG. 2, the use of anti-RNAI to increase plasmid production is illustrated.

Figure 3A:
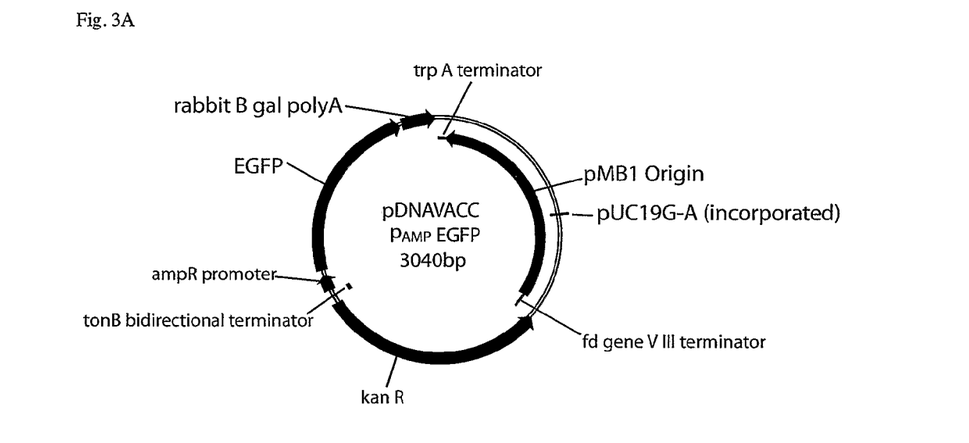
FIG. 3: shows the pDNAVACC-$P_{AMP}$-EGFP Reporter and pEDF-antiRNAI(10-108)3x plasmids.
Figure 3B:
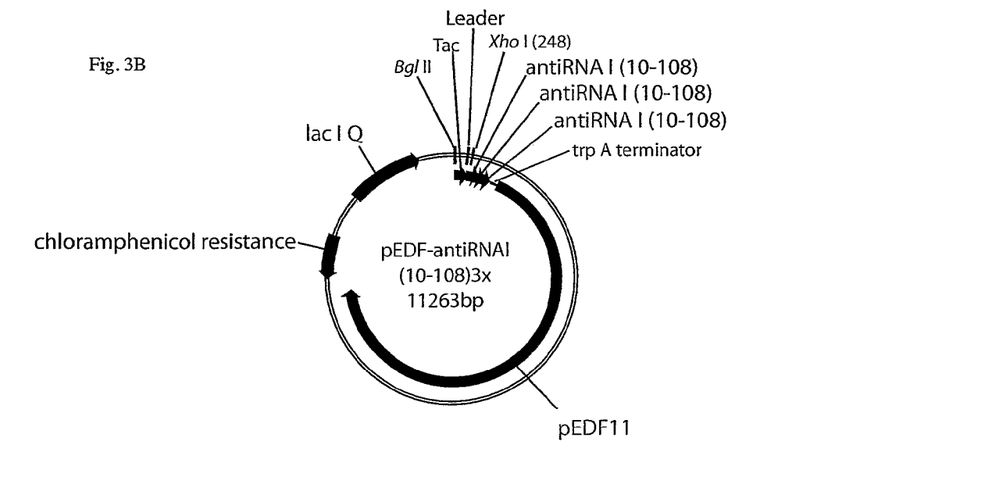
Figure 4:
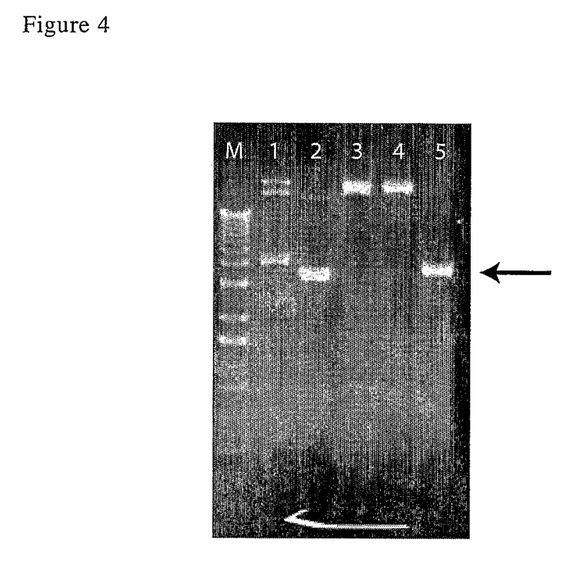
FIG. 4: shows plasmid induced by anti-RNAI is of a high quality.
Table 1: Host strains
Table 2: Anti-RNAI induced target plasmid production
Table 3: Anti-RNAI induction of plasmid copy number in DH10B
Table 4: Anti-RNAI induction of plasmid copy number in DH5α

In FIG. 3, the (A) pDNAVACC-$P_{AMP}$-EGFP Reporter and (B) pEDF-antiRNAI(10-108)3x plasmids are shown FIG. 4: the quality of plasmid induced by anti-RNAI induction is shown by agarose gel analysis. 1 ug of plasmid DNA prepared from induced cultures of DH10B cells containing the indicated plasmids, was resolved on 1% agarose gel. DNA was detected by pre-staining with SYBR Green I (Molecular Probes). M=Invitrogen 1 kb DNA ladder. Lane 1=pBR322+ pEDF-RNAI(10-108); Lane 2=pBR322+pEDF-antiRNAI (10-108); Lane 3=pEDF-RNAI(10-108); Lane 4=pEDF-antiRNAI(10-108); Lane 5=pBR322. The lower band (arrow) in lanes 1, 2 and 5 is supercoiled monomeric pBR322. The retarded mobility in lane 1 is an artifact of SYBR Green I prestaining of low amounts of supercoiled DNA. The larger bands in lanes 1-4 are a mixture of genomic DNA and the pEDF plasmids.

Definitions

Anti-RNAI: A molecule that interferes with the copy number repressive function of RNAI and or promotes the priming ability of RNAII. Anti-RNAI may be a RNA, protein, peptide, metabolite or small molecule or chemical that inhibits the function of RNAI. An inhibitory RNA may be a single stranded RNA, double stranded RNA, hairpin RNA, microRNA, RNA aptamer or ribozyme or any or all combinations thereof. For example, an antisense RNA may be a fragment of RNAII that corresponds to part (e.g. 10-108 of RNAI) or all (e.g. 1-108 of RNAI) of the three loop region of homology between RNAI and RNAII.

Anti-RNAI(1-108): A fragment of RNAII that corresponds to all 108 by of the three loop region of homology between RNAI and RNAII.

Anti-RNAI(10-108): A fragment of RNAII that corresponds to part (10-108 of RNAI) of the three loop region of homology between RNAI and RNAII, deleting bases 1-9 of RNAI (corresponding to RNAI sequence ACAGTATTT that contain the RNaseE cleavage site between the TA (UA in the RNAI).

ccc: Covalently Closed Circular

ColE1 derived origin: Origin of replicated derived from ColE1 type plasmid (e.g. pMB1, ColE1) by deletion (e.g. pBR322 derived origin) and/or base change (e.g. pUC from pMB1, pMM1, pMM5, pMM7 from ColE1)

DNA replicon: plasmids, cosmids, bacterial artificial chromosomes (BACs) bacteriophages, viral vectors and hybrids thereof pDNA: Plasmid DNA pBR322 origin: pMB1 origin from pBR322, in which the rop (repressor of primer) gene is present pBR322-derived origin: pMB1 origin from pBR322, in which the rop (repressor of primer) gene has been deleted plasmid: plasmids, cosmids, bacterial artificial chromosomes (BACs), bacteriophages, viral vectors and hybrids thereof pUC origin: pBR322-derived origin, with G to A transition that increases copy number at elevated temperature RESL: restriction enzyme selected ligation, to produce directional head to tail concatamers rop: or rom, is repressor of primer protein, that reduces copy number by stabilizing the RNAI: RNAII interaction The invention relates to methods for production of covalently closed circular (ccc) recombinant DNA molecules such as plasmids, cosmids, bacterial artificial chromosomes (BACs), bacteriophages, viral vectors and hybrids thereof (herein collectively referred to as plasmids) in a bacterial production host.

The invention is a cost effective method for improving yield of plasmid DNA during culture. Disclosed herein are bacterial strains with inducible factors that cause increased plasmid replication and dramatically improve productivity by a synergistic interaction with existing high copy origins. These systems would preferably be inducible at the end of fermentation to limit plasmid mediated metabolic burden during growth, and to reduce potential toxicity effects.

Plasmid Production Process Preferred Embodiments

The most specific method for inducible plasmid runaway replication, without inherently changing plasmid replication and DNA repair processes (that could alter plasmid quality), is controlled overexpression (to limit plasmid mediated metabolic burden during growth) of a potent specific activator(s) of plasmid replication. Rationally designed antisense inhibitors of RNAI that are more potent than the existing spurious inhibitors (e.g. tRNAs) are disclosed herein that facilitate dramatically increased productivity utilizing existing high copy number ColE1 plasmids (Tables 2, 3 and 4).

In one preferred embodiment for production of ColE1 derived origin containing plasmids, plasmid copy number is increased by inducible production of anti-RNAI regulators. This process dramatically improves plasmid DNA yield, while maintaining plasmid integrity, relative to the processes described in the art.

Using this process with moderate copy plasmids (e.g. pBR322 replication origin, with ROP gene deleted, herein referred to as pBR322-derived plasmids), plasmid yields are improved up to 5 fold.

Using this process with high copy plasmids (e.g. pUC origin), plasmid yields are improved up to 3 fold.

In one preferred embodiment for production of temperature inducible DNA replicons (e.g. pUC or pMM1 origin containing plasmids) the plasmid is produced by batch or fed batch fermentation. The fermentation may be performed utilizing methodologies described in the art (Reviewed in Carnes Supra 2005). For example, fed batch fermentation may be performed at restricted cell growth rate and reduced temperature during the growth phase; plasmid production may then be induced by temperature up shift and anti-RNAI induction.

This novel strategy for high yield plasmid production of high-copy origin containing plasmids (e.g. pUC origin) disclosed herein results in the new and unexpected observation of amplification of plasmid copy number even with existing high copy plasmids. One possible mechanism for how the process functions to increase copy number is shown in FIG. 2. This new combination of elements (antisense inducer that is not plasmid encoded combined with a high copy target plasmid) is physically different from existing strategies described in the art, has not previously been applied to the production of ColE1 derived origin plasmids, and when tested gave the new and unexpected result of improved productivity without loss of quality with existing high copy plasmids. The result is unexpected, since the art teaches that the pUC G to A transition in high copy plasmids makes the RNAII molecule resistant to inhibition by RNAI regulation (Lin-Chao et al, Supra, 1992). Consistent with this, existing copy number enhancing chromosomal mutations were all selected with moderate copy number pBR322 based plasmids and have not been shown to improve copy number with high copy pUC origin containing plasmids. We speculate that perhaps the anti-RNAI molecules of the invention also enhances RNAII priming efficiency, through an unknown mechanism, to account for the unexpected increase in copy number of high copy plasmids such as pUC19. An investigator of average skill in the art would therefore not attempt this strategy to improve productivity with high copy plasmids. Thus, we teach a new use (improved productivity) for the new combination of elements (antisense RNA combined with a high copy target plasmid) for induction of plasmid production, the success of which is contrary to prior art teaching.

Anti-RNAI Preferred Embodiments

Anti-RNAI may be a RNA, protein, peptide, metabolite or small molecule or chemical that inhibits the function of RNAI. An inhibitory RNA may be a single stranded RNA, double stranded RNA, hairpin RNA, microRNA, RNA aptamer or ribozyme or any or all combinations thereof.

In one preferred embodiment anti-RNAI is an antisense regulator of RNAI. In a preferred embodiment, anti-RNAI is anti-RNAI(1-108) which is a fragment of RNAII that corresponds to all 108 by of the three loop region of homology between RNAI and RNAII.

In yet another preferred embodiment, anti-RNAI is anti-RNAI(10-108) which is a fragment of RNAII that corresponds to part (10-108 of RNAI) of the three loop region of homology between RNAI and RNAII, deleting bases 1-9 of RNAI (corresponding to RNAI sequence 5' ACAGTATTT 3' that contain the RNaseE cleavage site between the TA (UA in the RNAI). In yet another preferred embodiment, anti-RNAI is Anti-RNAI(10-108)x or Anti-RNAI(1-108)x, wherein x denotes multimers of antiRNAI(10-108) from 1 to 20, and preferably from 1 to 4.

Expression of an anti-RNAI protein, peptide or RNA may be driven by constitutive or, more preferably, inducible promoters. Inducible promoters that are preferred include, but are not limited to, lambda PR and PL, other phage promoters such as T5, T7, synthetic promoters such as tac and trc, endogenous promoters such as lac, cold shock promoters (cspA), araBAD, stationary phase or starvation promoters, growth rate (rmf) pH (cadA) or anoxia responsive (nar) promoters. Induction can be by increased temperature (PL, tac), decreasing temperature (cspA; cold shock promoter) with thermostable repressors (lambda repressor, lac repressor), inducers (IPTG for tac, trc and lac; Arabinose for AraBAD) or other means (e.g. entry into stationary phase, pH or oxygen shift, glucose or amino acid starvation; reviewed in: Makrides S C. 1996 *Microbiol. Rev.* 60:512-538). Alternatively, the gene may be induced by a regulated antisense RNA.

Target Plasmid and Host Strain Preferred Embodiments

We contemplate use of the invention in the production of plasmids with a variety of pMB1 or ColE1 derived origins of replication, that are either high copy, low copy and moderate copy, and are either temperature inducible or not. This includes a non limiting list of therapeutic plasmids, such as pMB1 derived pUC origin containing pDNA3, VR1012, pVAX1, pVC0396, ColE1 derived pMM1 origin containing pVC0396 or pBR322-derived origin containing pCMVkm2.

The anti-RNAI gene can be in a plasmid that is compatible with the target plasmid, or most preferably integrated into the genome. Strain engineering can be performed in any strain of bacteria that is suitable for plasmid production.

Strains of bacteria bearing integrated copies of anti-RNAI expression cassettes are made using a variety of techniques, for example lambda red gam recombination (Murphy K C 1998 J. Bact. 180: 2063-2071; Datsenko K A, Wanner B L. 2000 Proc. Natl. Acad. Sci. (USA); 97:6640-6645). This technique has been utilized successfully in recA-strains such as DH5α, a common plasmid production host. Briefly, the expression cassette (s) including a flanking antibiotic resistance gene is PCR amplified using primers containing sequences homologous to the integration site. The target DH5α strain is transformed with the ampicillin resistant lambda Red recombination function containing plasmid pKD46 and Red recombinase production induced with arabinose. The cells are prepared and electroporated with the PCR fragment as described. Homologous recombinants are selected with kanamycin and cured of the pKD46 helper plasmid by shifting to the non-permissive temperature (pKD46 has a temperature sensitive origin of replication) and loss of ampicillin resistance verified.

Alternative host strains are contemplated. E. coli strain DH5α is a widely used host for plasmid production. Its key qualities include the recA mutation, which minimizes non-specific recombination of cloned DNA, and the endA1 mutation, eliminating non-specific digestion of plasmid by Endonuclease I. In addition to DH5α, a variety of other strains are suited for plasmid production; a non limiting list of exemplary E. coli host strains is shown in Table 1.

Production of Unstable Plasmids

We also contemplate use of the invention in the production of plasmids containing unstable sequences. Palindrome sequences, direct or inverted repeats, and Z DNA forming sequences are unstable and are deleted or rearranged by E. coli hosts. In some instances, plasmids for therapeutic use must contain unstable sequences (inverted or direct repeats for viral vectors such as AAV and HIV, Z DNA forming segments or triplet repeats for certain therapeutic genes). Current strategies to maintain plasmids containing unstable sequences are to use host cell lines with stabilizing mutations. Several hosts are commercially available for propagation of these plasmids, for example, Sure cells (Stratagene), GT115 (Invivogen) or Stbl2 and Stbl4 (Invitrogen). The Stbl2 and Stbl4 cell lines utilize an undisclosed mutation that increases stability of direct repeat containing vectors such as retroviral vectors; this effect is enhanced at reduced temperature, presumably due to reduced copy number. Specific combinations of repair mutations can stabilize plasmid propagation, especially at low temperature. The Sure and Sure2 cell lines uses one such combination, with homologous recombination deficiency (recB, recJ) in conjunction with UV repair (uvrC) and SOS repair (umuC) deficiency (to stabilize LTRs), and SbcC (and recJ) to stabilize Z DNA. The GT116 cell line uses SbcC

TABLE 1

Host strains

| Strain | Genotype | Source |
|---|---|---|
| DH1 | recA1 endA1 hsdR17(rk−, mk+) phoA supE44 λ− thi-1 gyrA96 relA1 | Invitrogen |
| DH5α | F− Φ80dlacZΔM15 Δ(lacZYA-argF) U169 recA1 endA1 hsdR17(rk−, mk+) phoA supE44 λ− thi-1 gyrA96 relA1 | Invitrogen |
| DH10B | F− mcrA Δ(mrr-shdRMS-mrcBC), Φ80lacZΔM15 ΔlacZ74, deoR, recA1, endA1, araD139, Δ(ara-leu)7697, galU, galK, λ−, rpsL, nupG | Invitrogen |
| JM109 | endA1, recA1 gyrA96, thi, hsdR17(rk−, mk+) relA1, supE44 Δ(lac-ProAB) [F'traD36, proAB lacI$^q$ZΔM15] | Stratagene |
| XL1-Blue | recA1 endA1 gyrA96 thi-1 hsdR17 supE44 relA1 lac [F'proAB lacI$^q$ZΔM15 Tn10 (Tet$^r$)] | Stratagene |
| Top10 | F− mcrA Δ(mrr-hsdRMS-mcrBC) Φ80lacZΔM15 ΔlacX74 recA1 araΔ139 Δ(ara-leu)7697 galU galK rpsL (Str$^R$) endA1 nupG | Invitrogen |
| Mach1 | ΔrecA1398 endA1 tonA Φ80ΔlacM15 ΔlacX74 hsdR($r_k^-m_k^+$) | Invitrogen |
| GT116 | F− mcrA Δ(mrr-hsdRMS-mcrBC) Φ80lacZΔM15 ΔlacX74 recA1 endA1 Δdcm ΔsbcC-sbcD | Invivogen |
| ECOS101 | F− (Φ80 ΔlacZ ΔM15)Δ(lacZYA-argF)U169 hsdR17($r_{K-}$ $m_{K+}$) recA1 endA1 relA1 deoR λ− | Yeastern |
| EC100 | F− mcrA Δ(mrr-hsdRMS-mcrBS) Φ80 ΔlacZ ΔM15)ΔlacX74 recA1 endA1 araD139(ara, leu)7697, galU, galK, λ− rpsL, nupG | Epicentre |
| Sure | e14− (McrA−) Δ (mcrCB-hsdSMR-mrr)171 endA1 supE44 thi-1 gyrA96 relA1 lac recB recJ sbcC umuC::Tn5 (Kan$^r$) uvrC [F' proAB lacI$^q$Z□M15 Tn10 (Tet$^r$)] | Stratagene |
| Stbl2 | F− mcrA Δ(mcrBC-hsdRMS-mrr) recA1 endA1 lon gyrA96 thi supE44 relA1 λ− Δ(lac-proAB) | Invitrogen |
| Stbl4 | mcrA Δ(mcrBC-hsdRMS-mrr) recA1 endA1 gyrA96 gal− thi-1 supE44 λ− relA1 Δ(lac-proAB)/F'proAB+ lacI$^q$ZΔM15 Tn10 Tet$^R$ | Invitrogen |

DH5α, XL1-Blue, DH10B, JM109 and Top 10 have been well established as plasmid production strains. Mach1, and ECOS101 have been developed recently and may be desirable plasmid production hosts. Stbl2, GT116 and Sure cells have been utilized for the production of unstable DNA containing plasmids. Unstable DNA contains structures like direct (e.g. retroviral long terminal repeats) or inverted repeats (e.g. shRNA palindromes), Z DNA, etc. The deletion of the dcm gene in GT116 eliminates dam methylation which is immuno-stimulatory. Therefore, production in GT116 reduces the immunogenicity of plasmid DNA. Similar reductions in immunogenicity are observed utilizing strains expressing CpG methylase.

and SbcD to stabilize palindromic sequences. These strains function to stabilize plasmids only at low temperature (i.e. 30° C.), presumably due to reduced plasmid copy number. This strategy obviously increases production cost. Use of the inducible process described herein would allow propagation at 30° C. of unstable plasmids in stabilizing cell lines, prior to increasing copy number only for a short duration prior to harvest using Anti-RNAI. This should maximize yield and stability (i.e. quality) of unstable plasmids.

Improvement to Final Product Purity

We contemplate utilizing plasmid enriched feed streams resulting from use of the disclosed invention in exemplary plasmid purification processes. Such processes are well known in the art. The combination of high yield fermentation and exemplary purification process may provide cost effective methodologies to further reduce genomic DNA to acceptable levels for gene therapy and DNA vaccination applications.

EXAMPLES

The method of the invention is further illustrated in the following examples. These are provided by way of illustration and are not intended in any way to limit the scope of the invention.

Example 1

Creation of pEDF11-RNA Expression Plasmids

RNA Expression Vector

A Tac promoter expression plasmid was created for stable expression of RNA by: 1) Deletion of the Ribosome binding site-cloning region leaving a XhoI cloning site and 2) Insertion of TrpA transcriptional terminator annealed oligonucleotides at the XhoI site.

The RNA expression region encodes an 5' end hairpin loop formed by the lac operator-flanking sequence (start 5' AATTGTG 3' to 5' CACAATT 3' end) and has the TrpA terminator hairpin loop (start 5' GCCCGC 3' to 5' GCGGGC 3' end) at the 3' end. These stabilizers should limit RNaseE and RNaseIII exodigestion, to increase transcript stability.

The structure of the RNA expressed from the parent vector is:

(5'Hairpin loop)-<u>CTCGAG</u>-(3' Terminator Hairpin loop)
            XhoI The target antisense RNA's were cloned between the two loops using the unique XhoI site. The structure of the antisense RNA expressed from the vector is:

(5'Hairpin loop)-<u>CTCGAG</u>-anti-RNAI-<u>GTCGAG</u>-(3' Terminator Hairpin loop)
            XhoI          (SalI/XhoI)

The pVEX1 encoded hairpin loops flanking the antisense RNA's were designed to not inhibit antisense repression. Plasmid copy number control antisense hybrids do not form between the entire sequences due to steric constraints; rather the loop-loop interaction progresses to a stable four-way junction (Kolb F A, Engdahl H M, Slagter-Jager J G, Ehresmann B, Ehresmann C, Westhof E, Wagner E G, Romby P. 2000. *EMBO J.* 19:5905-15). All single insert constructs were predicted to fold correctly into the specified anti-RNAI loops with flanking stabilizing loops using the mfold version 3.1 RNA folding program (Zuker, M. 2003 *Nucleic Acids Res.* 31:3406-15). Multimer inserts are predicted to have complex folding.

RNA was expressed from a low copy (approximately 10 copies per cell) RSF1010 derived replication origin (compatible with ColE1). This replication origin is not regulated by antisense RNA and its copy number will not be affected by the encoded antisense RNAs. The replication origin was obtained as a 7.6 kb PstI/SacI fragment from pEDF11 (Diaz E. Munthali M. Lunsdorf H. Holtje J V. Timmis K N. 1996 *Mol. Microbiol.* 19: 667-681). This fragment contains the replication functions of the pNM185 parent plasmid (Mermod N, Ramos J L, Lehrbach P R, Timmis K N. 1986 *J. Bacteriol.* 167: 447-454). The Tac promoter expression element was PCR amplified with primers containing PstI and SacI sites (for cloning into the pEDF11 PCR product) that amplified a 3.3. kb fragment that contained the pACYC184 chloramphenicol resistance gene, the lacIQ gene and the RNA expression element. The final construct (pEDF-pVEX1) was confirmed by restriction mapping.

Example 2

Creation of pWizBang 2.0-RNAI pWizBang 2.0

In order to facilitate the ordered, directional assembly of genes and vectors, we devised a new vector for a modular approach, in which each DNA fragment is assigned two unique, non-palindromic address tags. This method relies upon the ability of class IIS restriction enzymes to digest at a distance from the enzyme site. Blunt DNA fragments (synthetic dsDNA; PCR amplicons; or blunt restriction fragments) are cloned into a SmaI site of the vector, PWizBang 2.0 (Nature Technology Corporation, Lincoln, Nebr.), and the class IIS enzyme AarI (a seven base cutter commercially available from Fermentas, or an AarI isoschizomer, is used to cleave the DNA, leaving a four base, 5'-overhang precisely beginning and ending at the cloning site (i.e., the first and last bases of the 4 base overhangs correspond to the first and last bases of the insert). The fragments are recovered and used in ligation reactions.

pWizBang 2.0-RNAI Constructs

Individual antisense modules were created using filled overlapping oligonucleotides and cloned into pWizBang 2.0 as blunt fragments and sequenced. The inserts were designed to facilitate directional cloning of single fragments, or fragment multimers utilizing Restriction Fragment Selected Ligation (RESL). In this strategy, the 5' and 3' ends of each insert incorporate the last 5 by of XhoI and SalI, respectively. These restriction enzymes recognize heterologous sequences, but create the same 4 by sticky end. AarI digestion of the pWizBang 2.0 clone released the unit with these sticky ends. The fragments were purified, and cloned directly into the pEDF11-pVEX1 expression vector cleaved with XhoI restriction enzyme and dephosphorylated. Orientation was determined by XhoI digestion since only the 5' end of the insert can regenerate the XhoI site. The insert was directionally concatamerized by ligation in the presence of the pair of restriction enzymes. This methodology (RESL) created a ladder of orientation specific head to tail concatamers that were gel purified (with a broad range of concatamer number) and cloned into the pEDF11-pVEX1 vector. Isolated vectors were confirmed by sequencing.

Example 3

Creation of pEDF-RNAI Antisense Constructs

Two sets of RNAI antisense constructs were created, targeting:
  i) the entire region of homology (residues 1-108)
  ii) the loop structure (residues 10-108) deleting the RNaseE cleavage site Both clones are identical to the RNAII primer, through the region of homology. The RNAII primer is expressed at low level with alternative folding conformations (mediated by downstream sequences) that do not bind RNAI.

Initial comparative evaluation of 1-108 and 10-108 demonstrated both constructs could induce pMB1 reporter plasmid copy number. Due to a slightly improved induction observed with the 10-108 clone, this clone was selected for further analysis.

The inserts were cloned in both orientations in pEDF-pVEX1. The sense orientation was a control for each plasmid, as well as the parent pEDF-pVEX1. Multimer inserts were also created.

Directional multimers of antisense RNAI created by RESL were also created (Example 5). One such multiple, an 3x anti-RNAI(10-108) insert is shown (pEDF-antiRNAI(10-108)3x; FIG. 3b).

Example 4

Improved Plasmid Yield Using pEDF-RNAI Antisense Constructs

The pEDF-antiRNAI(10-108) and control pEDF-RNAI (10-108) plasmids were transformed into the DH10B cell line with or without the pMB1 origin containing target plasmids pBR322 (moderate copy number; contains the ROP gene and does not contain the high copy pUC G to A mutation) or pUC19 (high copy number). Cultures were grown in LB media and RNA production induced with 1 mM IPTG. Plasmid was quantified by miniprep (Qiagen miniprep columns) using 5 $OD_{600}$ of cells (to standardize and prevent column overloading). In both cases, >3 fold induction of target plasmid levels was observed, compared to either pUC19 or pBR322 alone, when the antiRNAI(10-108) construct was induced. The results for pBR322, shown in Table 2, demonstrate the >3 fold improvement in plasmid yield. Yield with pUC19 was increased 8 fold from 1.4 ug/5$OD_{600}$ cells with pUC19 to 10.8 ug/5$OD_{600}$ cells with pUC19+ antiRNAI(10-108)) The induced plasmid (pBR322 or pUC) was of a high quality (FIG. 4). This demonstrates that antiRNAI(10-108), expressed separate from a target plasmid, can induce the production of high quality supercoiled pMB1 derived origin containing plasmids.

TABLE 2

Anti-RNAI induced target plasmid production

| pEDF plasmid | pBR322 plasmid | Experimental | ug/5$OD_{600}$ cells |
|---|---|---|---|
| RNAI(10-108) | pBR322 | Sense RNA control | 3.4 |
| antiRNAI(10-108) | pBR322 | Antisense RNA | 11.3 |
| RNAI(10-108) | | Plasmid control | 1.5 |
| antiRNAI(10-108) | | Plasmid control | 1.4 |
| | pBR322 | Plasmid control | 3.0 |

Example 5

Fluorescent Reporter Plasmids

To facilitate high throughput evaluation of copy number, fluorescence reporter plasmids were constructed, and linearity of fluorescence with copy number verified. EGFP was used as the fluorescence marker, since it has been validated as a surrogate marker for quantification of copy number alterations (Magliery T J, Regan L. 2004 *Protein Engineering, design selection* 17:77-83). A derivative of the existing nonfluorescent pDNAVACC-EGFP plasmids, with EGFP expression driven by a low level constitutive ampicillin gene promoter ($P_{AMP}$) was constructed by insertion of PCR amplified $P_{AMP}$ from pUC plasmid into NcoI/XbaI cleaved pUC origin pDNAVACC-EGFP plasmid. The PCR amplified $P_{AMP}$ promoter was cloned into pWizBang 2.0 and sequence verified, and excised with NcoI and)(bat The NcoI site contains the ATG start codon (CC<u>ATG</u>G) of the EGFP gene. Fluorescence from this plasmid was undetectable. This was improved by PCR based insertional mutagenesis. The entire plasmid was PCR amplified using AarI containing PCR primers that, upon AarI digestion, generated compatible non-palindromic 4 bp sticky ends that afforded recircularization of the vectors. The PCR primers contained additional sequences that introduced the bacteriophage T7 gene 10 ribosome binding site and spacer immediately upstream of the ATG start codon of the EGFP gene, and directly downstream of the $P_{AMP}$ promoter. The resultant construct, pDNAVACC $P_{AMP}$-EGFP is shown in FIG. 3a. This construct produced detectable fluorescence. A derivative, pDNAVACC $P_{AMP}$-EGFP (short origin) contains a minimal 600 by pUC origin; this was made by transfer of the BglII/XbaI $P_{AMP}$-EGFP containing fragment. A second derivate with a pBR322-derived origin (ROP-origin similar to pUC, but without the pUC G to A mutation) was also constructed (pBR322-derived $P_{AMP}$-EGFP).

Fluorescence was determined using a BioTek FLx800 microplate fluorescence reader. Linearity of fluorescence with copy number (ug plasmid obtained using Qiagen minipreps) was verified, using conditions that produce high and low copy numbers (i.e. wild type DH5α and pcnB GBE180 hosts, at 30 and 37° C.) in LB or MOPS minimal media (Neidhardt F C, Bloch P L, Smith D F. 1974 *J Bacteriol*. 119: 736-747) using glycerol as carbon source (to mimic fermentation media).

Example 6

Screening for Antisense RNAI Inhibitors Useful for the Production of Plasmids

The pBR322-derived $P_{AMP}$-EGFP reporter plasmid was cotransformed with the pEDF-antiRNAI(10-108) construct, pEDF-RNAI(10-108) control construct or ligations of monomer antiRNAI(10-108) or RESL generated antiRNAI(10-108) multimers into the XhoI site of the pEDF-antiRNAI(10-108). The ligations and plasmids were transformed into DH10B, plated onto LB plates with or without IPTG, and grown at 30° C. or 37° C. Colonies were screened for improved fluorescence versus the pEDF-antiRNAI(10-108)+ pBR322-derived $P_{AMP}$-EGFP reporter control. Strongly fluorescent colonies were identified, and inserts sequenced. From this screen, 2x, 3x, 3.5x (deletion of part of 4th copy) and 4x antiRNAI(10-108) were isolated and shown to induce the pBR322-derived $P_{AMP}$-EGFP reporter plasmid copy number.

Fragments of anti-RNAI, corresponding to either loop 1, loop 2, or loop 3 or the partial loop 3 antisense of Sarkar et al, Supra, 2002 were made by ligation of annealed complementary primers into the XhoI site of pEDF-pVAX1. The ligations were cotransformed with 1) the pBR322-derived $P_{AMP}$-EGFP or 2) pDNAVACC $P_{AMP}$-EGFP (short origin), transformed into DH10B and screened for improvement of target plasmid copy number (increased fluorescence). No improvement of fluorescence was observed. This demonstrates that the putative antisense regulator reported by Sarkar et al, Supra, 2002 does not function to increase the copy number of moderate or high copy plasmids.

Example 7

Improved Plasmid Yield Using pEDF-RNAI Multimer Antisense Constructs

The isolated pEDF-RNAI(10-108)x plasmids from Example 6 were cotransformed with the three fluorescent reporter constructs into both the DH5α and DH10B cell lines, and grown in LB media at 37° C., with or without 1 mM IPTG induction. Plasmid specific yield (ug plasmid per $OD_{600}$) and specific fluorescence (fluorescence units per $OD_{600}$; this demonstrates increased yield is due to amplification of the target reporter plasmid, not the RNAI plasmid) were determined, and are summarized in Tables 3 and 4.

Induction of plasmid copy number was observed after IPTG induction in both cell lines. Some increases without induction may be attributable to leaky expression of the tac promoter. Different numbers of (10-108) inserts (from 1-4x) all induce plasmid copy number increases, with both reporter cell lines. The degree of induction varies with the reporter plasmid, the host strain, and the number of inserts on the plasmid. With DH10B, up to 10 fold induction in reporter plasmid copy number ($FU/OD_{600}$) was observed. The more moderate induction with DH5α may be due to lower overall capacity for plasmid, or reduced amplification in stationary phase, compared to DH10B. The relA mutant DH5α will show the "relaxed response" in stationary phase, wherein uncharged tRNAs act to increase plasmid production yield. However, the observed higher level induction (and overall plasmid amount) in DH10B, and the moderate induction in stationary phase DH5α (up to 3 fold with pBR322-derived reporter, up to 45% increase with pUC based reporters) over and above the relA mediated tRNA moderated induction in DH5α demonstrates the antiRNAI(10-108)x inducers are more potent than the existing uncharged tRNA inducers in DH5α, or stationary phase inducers (such as amino acid starvation) in relA+DH10B. This demonstrates the anti-RNAI plasmid induction method of the invention improves plasmid yield significantly better than existing plasmid amplification methods based on stationary phase metabolic alterations described in the art.

TABLE 3

Anti-RNAI induction of plasmid copy number in DH10B***

| Cell line + | $OD_{600}$ | $FU/OD_{600}$* | µg $DNA/OD_{600}$** |
|---|---|---|---|
| Control plasmid + Reporter #1 | 2.245/2.095 | 992.13/873.67 | 1.45/1.14 |
| 1× insert plasmid + Reporter #1 | 2.32/1.995 | 1253.31/3357.73 | 1.72/3.13 |
| 2× insert plasmid + Reporter #1 | 2.3/1.64 | 1479.57/6691.46 | 2.26/5.12 |
| 3× insert plasmid + Reporter #1 | 2.21/1.595 | 1705.88/5586.21 | 2.53/4.01 |
| 3.5× insert plasmid + Reporter #1 | 2.26/1.255 | 1828.46/7017 | 2.48/5.42 |
| 4× insert plasmid + Reporter #1 | 2.235/1.555 | 1762/4945.34 | 2.75/3.12 |
| Control plasmid + Reporter #2 | 2.14/1.945 | 1606.23/1575.32 | 2.73/2.6 |
| 1× insert plasmid + Reporter #2 | 2.25/1.98 | 1727.41/3144.61 | 3.02/4.6 |
| 2× insert plasmid + Reporter #2 | 2.725/1.95 | 869/3670.1 | 1.61/3.74 |
| 3× insert plasmid + Reporter #2 | 2.24/1.7 | 1334.23/4801.76 | 1.18/2.12 |
| 3.5× insert plasmid + Reporter #2 | 2.475/2.4 | 842.15/1233.05 | 1.66/2.29 |
| 4× insert plasmid + Reporter #2 | 2.005/1.33 | 1755.28/8431.35 | 3.84/7.44 |
| Control plasmid + Reporter #3 | 2.16/1.885 | 526.54/367.46 | 1.13/.584 |
| 1× insert plasmid + Reporter #3 | 2.355/1.985 | 651.94/1190.77 | 2.06/1.81 |
| 2× insert plasmid + Reporter #3 | 2.25/1.955 | 671.48/778.86 | 1.96/1.89 |
| 3× insert plasmid + Reporter #3 | 2.165/1.015 | 849.11/3310.67 | 2.36/2.17 |
| 3.5× insert plasmid + Reporter #3 | 2.06/1.34 | 842.88/4206.22 | 2.21/4.81 |
| 4× insert plasmid + Reporter #3 | 2.195/2.12 | 1087.02/1086.95 | 2.71/2.57 |

*FU = Fluorescence Units
**Specific Yield = ug DNA from 1.0 $OD_{600}$
***(all numbers are without IPTG/with IPTG induction)
+ Reporter 1 = pBR322-derived $P_{AMP}$ – EGFP,
Reporter 2 = pDNAVACC $P_{AMP}$ – EGFP (short origin),
Reporter 3 = pDNAVACC $P_{AMP}$ – EGFP.
Control plasmid = pEDF-RNAI(10-108),
Insert plasmids contain pEDF-antiRNAI(10-108)$_n$ where n = 1, 2, 3, 3.5 or 4× copies of antiRNAI(10-108)

TABLE 4

Anti-RNAI induction of plasmid copy number in DH5α***

| Cell line | $OD_{600}$ | $FU/OD_{660}$* | µg $DNA/OD_{600}$** |
|---|---|---|---|
| Control plasmid + Reporter #1 | 2.89/2.835 | 689.07/854.94 | .88/1.27 |
| 1× insert plasmid + Reporter #1 | 2.63/2.43 | 1866.83/2722.26 | 1.54/2.78 |
| 2× insert plasmid + Reporter #1 | 2.4/1.675 | 2521.98/3756.46 | 2.27/2.06 |
| 3× insert plasmid + Reporter #1 | 2.41/1.7 | 2751.63/3212.21 | 2.41/3.65 |
| 3.5× insert plasmid + Reporter #1 | 2.395/1.595 | 2837.19/3745.3 | 2.8/2.04 |
| 4× insert plasmid + Reporter #1 | 2.28/2.01 | 3082.5/3129.4 | 3.09/1.64 |
| Control plasmid + Reporter #2 | 2.785/2.405 | 816.31/829.42 | 1.53/1.64 |

TABLE 4-continued

Anti-RNAI induction of plasmid copy number in DH5α***

| Cell line | $OD_{600}$ | $FU/OD_{660}$* | μg $DNA/OD_{600}$** |
|---|---|---|---|
| 1× insert plasmid + Reporter #2 | 2.175/1.745 | 714.68/855.83 | 1.82/2.26 |
| 2× insert plasmid + Reporter #2 | 2.245/2.195 | 873.68/1015.38 | .98/2.85 |
| 3× insert plasmid + Reporter #2 | 2.145/1.805 | 496.07/906.6 | 1.98/3.3 |
| 3.5× insert plasmid + Reporter #2 | 2.485/2.515 | 833.7/397.25 | .724/.7 |
| 4× insert plasmid + Reporter #2 | 2.15/2.21 | 1010.73/607.73 | .884/1.43 |
| Control plasmid + Reporter #3 | 2.68/2.47 | 725.53/808.28 | 2.24/2.47 |
| 1× insert plasmid + Reporter #3 | 2.62/1.58 | 763/982.33 | 1.87/1.65 |
| 2× insert plasmid + Reporter #3 | 2.155/2.49 | 841.8/1172.32 | 1.37/3.59 |
| 3× insert plasmid + Reporter #3 | 2.06/2.15 | 846.48/620.35 | 1.17/1.63 |
| 3.5× insert plasmid + Reporter #3 | 2.04/2.455 | 903.3/493.45 | 1.08/1.43 |
| 4× insert plasmid + Reporter #3 | 2.06/2.345 | 1004.4/585.96 | 1.21/1.88 |

*FU = Fluorescence Units
**Specific Yield = ug DNA from 1.0 $OD_{600}$
***(all numbers are without IPTG/with IPTG induction)
+ Reporter 1 = pBR322-derived $P_{AMP}$ – EGFP,
Reporter 2 = pDNAVACC $P_{AMP}$ – EGFP (short origin),
Reporter 3 = pDNAVACC $P_{AMP}$ – EGFP.
Control plasmid = pEDF-RNAI(10-108),
Insert plasmids contain pEDF-antiRNAI(10-108)$_n$ where n = 1, 2, 3, 3.5 or 4× copies of antiRNAI(10-108)

Collectively, these results demonstrate the general utility the anti-RNAI compositions and processes of the invention to improve plasmid DNA productivity while maintaining quality. Production of anti-RNAI in a host cell line increases production of plasmids containing pMB1 type replication origins. This effect is not cell line specific (observed in DH5α and DH10B), nor specific to a particular anti-RNAI [amplification is seen with antiRNAI(1-108) and antiRNAI (10-108), and various concatamers of antiRNA(10-108)], nor specific to a particular replication origin (amplification seen with pBR322, pUC and pBR322-related origins). This demonstrates the general applicability of this method to improve production of plasmids containing a ColE1 type replication origin.

Thus, the reader will see that the compositions and production processes of the invention provide methods for improved plasmid production.

While the above description contains many specificities, these should not be construed as limitations on the invention, but rather as an exemplification of one preferred embodiment thereof. Many other variations are possible. For example, plasmid induction can be performed in fermentation culture. A variety of fermentation conditions have been developed (reviewed by Carnes, Supra, 2005) and are contemplated for use with the anti-RNAI regulators of the invention. For example, in an inducible fed-batch fermentation process, plasmid induction with anti-RNAI regulators can be utilized during the plasmid induction phase to further increase plasmid yield. The optimal temperature and degree of anti-RNAI induction, to maximize plasmid induction during the fed-batch phase can be determined by one skilled in the art. Accordingly, the scope of the invention should be determined not by the embodiments illustrated, but by the appended claims and their legal equivalents.

I claim:

1. A method for production of covalently closed supercoiled target plasmid DNA comprising a high copy number mutant ColE1 replication origin, the method comprising the steps of:
  A) growing bacterial cells containing the target plasmid DNA,
  B) increasing target plasmid replication by inducing expression in the bacterial cells of an anti-RNAI(10-108) comprising an antisense RNA complementary to the full length of RNAI residues 10-108, wherein said anti-RNAI(10-108) excludes ribozymes and is an antisense RNA selected from the group consisting of anti-RNAI(10-108), anti-RNAI (10-108)$_2$x, anti-RNAI (10-108)$_{3x}$, anti-RNAI (10-108)$_{3.5x}$, anti-RNAI (10-108)$_{4x}$, and wherein the anti-RNAI(10-108) is expressed from the bacterial genome or from a non-target plasmid, and
  C) continuing growth to accumulate target plasmid product; whereby said method increases plasmid yield relative to that obtained without expression of the anti-RNAI (10-108).

2. A composition of matter comprising a strain of bacteria comprising:
  A) an anti-RNAI(10-108) antisense inducer comprising an antisense RNA complementary to the full length of RNAI residues 10-108, wherein said anti-RNAI(10-108) excludes ribozymes and is an antisense RNA selected from the group consisting of anti-RNAI (10-108), anti-RNAI (10-108)$_2$x, anti-RNAI (10-108)$_{3x}$, anti-RNAI (10-108)$_{3.5x}$, anti-RNAI(10-108)$_{4x}$; and
  B) a target plasmid DNA comprising a high copy number mutant ColE1 replication origin, wherein the anti-RNAI (10-108) antisense inducer is used to improve the yield of the target plasmid obtained from culture.

* * * * *